United States Patent
Meakem

[11] Patent Number: 6,143,026
[45] Date of Patent: Nov. 7, 2000

[54] PROCESS FOR THE PRODUCTION OF A PROSTHETIC EYE

[76] Inventor: Thomas J. Meakem, 10215 Gainsborough Rd., Potomac, Md. 20854

[21] Appl. No.: 09/018,469

[22] Filed: Feb. 4, 1998

[51] Int. Cl.[7] .................................................. A61F 2/14
[52] U.S. Cl. ................................................. 623/4; 623/901
[58] Field of Search ........................................ 623/4, 901

[56] References Cited

U.S. PATENT DOCUMENTS

| | | | |
|---|---|---|---|
| 2,497,872 | 2/1950 | Erpf et al. | 623/4 |
| 2,692,391 | 10/1954 | Gougelman | 3/13 |
| 2,792,573 | 5/1957 | Clarke et al. | 3/13 |
| 3,679,504 | 7/1972 | Wichterle | 156/62 |
| 4,601,673 | 7/1986 | Nasca | 446/389 |
| 5,026,392 | 6/1991 | Gordon | 623/4 |
| 5,089,021 | 2/1992 | Vachet | 623/4 |
| 5,108,427 | 4/1992 | Majercik et al. | 623/4 |
| 5,108,776 | 4/1992 | Goldberg et al. | 427/2 |
| 5,130,160 | 7/1992 | Goldberg et al. | 427/2 |
| 5,345,309 | 9/1994 | Wertz et al. | 356/372 |
| 5,366,499 | 11/1994 | Py | 623/4 |
| 5,466,259 | 11/1995 | Durette | 623/4 |
| 5,522,887 | 6/1996 | Hoe | 623/4 |
| 5,526,285 | 6/1996 | Campo et al. | 364/526 |
| 5,540,612 | 7/1996 | Mendez | 446/392 |
| 5,556,427 | 9/1996 | Durette | 623/4 |
| 5,584,880 | 12/1996 | Martinez | 623/4 |
| 5,733,333 | 3/1998 | Sankey | 623/4 |

FOREIGN PATENT DOCUMENTS

| | | | |
|---|---|---|---|
| 456249 | 4/1949 | Canada | 623/4 |
| 265399 | 4/1988 | European Pat. Off. | 623/4 |
| 2339448 | 2/1975 | Germany | 623/4 |
| 3024795 | 4/1981 | Germany | 623/4 |
| 616263 | 1/1949 | United Kingdom | 623/4 |
| 624863 | 7/1949 | United Kingdom | 623/4 |
| 637540 | 5/1950 | United Kingdom | 623/4 |

*Primary Examiner*—Jeffrey A. Smith
*Attorney, Agent, or Firm*—Pillsbury Madison & Sutro LLP

[57] ABSTRACT

A method of preparing a prosthetic eye having a matching appearance of a natural eye by (a) taking an impression of the missing eye socket and evaluating soft tissue, (b) positioning a wax try in the socket for proper aperture and centering, (c) taking pictures of the natural eye using a high resolution camera and projecting the resulting pictures on a screen with color enhancement to obtain correct shades and color for the prosthetic, and (d) printing the color enhanced reproduction of the natural eye on the prosthetic, which is a material stable with acrylics, to obtain an exact duplicate of the natural eye. The information obtained from the natural eye can be stored and reproduced whenever required.

1 Claim, 1 Drawing Sheet

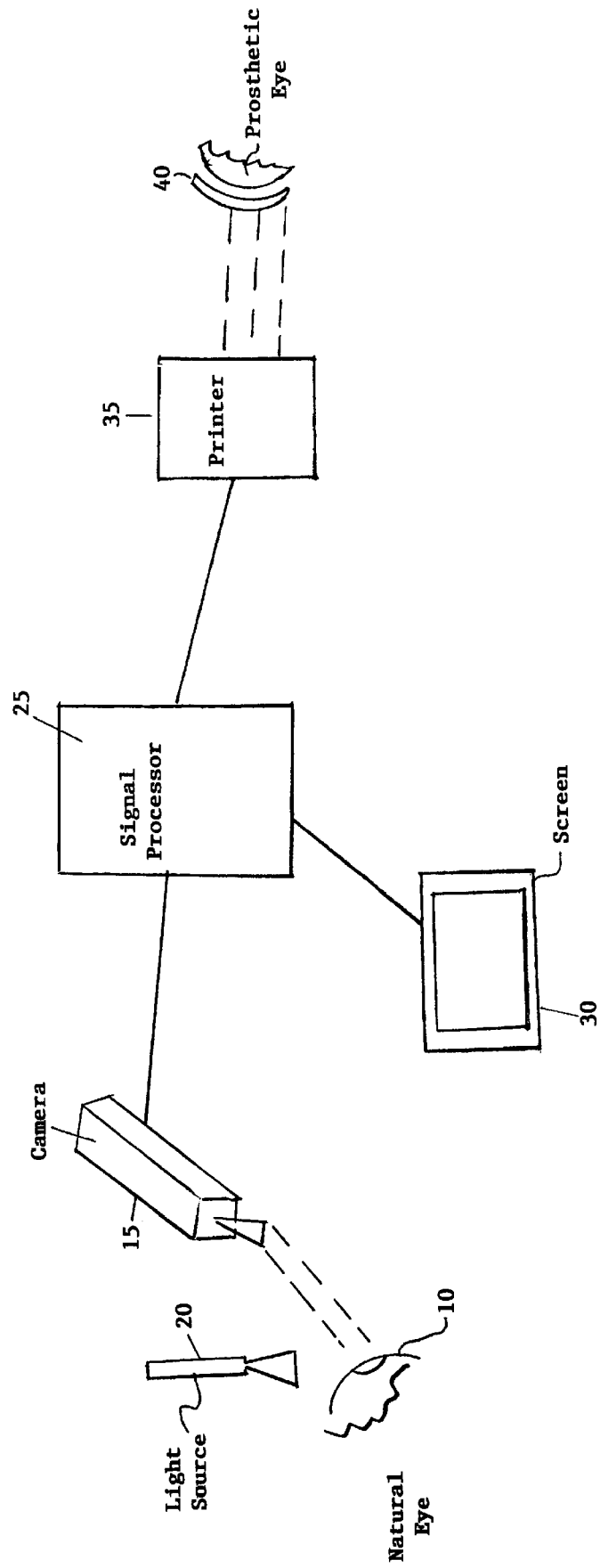

PROCESS FOR THE PRODUCTION OF A PROSTHETIC EYE

This invention relates to artificial eyes made of plastics and to a method by which prosthetic devices have characteristics matching the appearance of a natural eye.

BACKGROUND OF THE INVENTION

If a person can detect a difference between a person's eyes, the conclusion is immediate that one is artificial and it makes no difference which one is the artificial one, the purpose of having an artificial eye is largely lost both from a physical as well as a psychological viewpoint.

In artificial eye technique, the problem is one of matching colors and having an artificial eye look like the natural eye after color matching has been accomplished. Generally, the person who performs the fitting and color matching of the eye needs to be an artist in order to obtain an artificial eye that corresponds in appearance with that of the human eye.

The current procedure for the replacement of a missing eye involves (a) taking an impression of missing eye socket and evaluating the soft tissue, (b) placing a wax try in the eye socket for proper aperture and centering (c) painting the base prosthesis and utilizing the natural eye in an attempt to match all iris, scleral shades and veining and (d) placement of a clear layer of acrylic for the final surface and then delivering the completed prosthesis, with adjustments as needed or requested. This procedure requires a minimum of three appointments and does not necessarily result in obtaining an artificial eye which matches the remaining human eye in appearance.

An object of the invention is to provide a process for preparing a prosthetic eye which matches the remaining human eye in appearance.

Another object of the invention is obtain a consistent, reproductive, accurate reproduction of the natural eye.

A further object of the invention is to transfer the reproduction of the natural eye to a scleral base after computer three dimensional enhancement.

A still further object of the invention is to maintain a visible record on the computer of the patient's natural eye.

A further object of the invention is to be more efficient in prosthetic eye production saving the patient time and money.

Another object of the invention is to provide a prosthetic eye which can be completed and fitted with fewer appointments with the patient than present practice.

Other objects, aspects as well as the several advantages of the invention will be apparent to those skilled in the art upon reading the specification and the appended claims.

SUMMARY OF THE INVENTION

According to the invention, a process is provided for preparing a prosthetic eye comprising
 (a) taking an impression of the missing eye socket and evaluating soft tissue,
 (b) positioning a wax try in the socket for proper aperture and centering,
 (c) taking pictures of iris, sclera, etc. of the remaining eye with a digital camera;
 (d) projecting pictures on a screen with computer enhancement to verify shades and color, and
 (e) printing the color impression obtained from the natural eye onto an acrylic compatible material for placement on the prosthetic; and
 (f) placement of a finishing final coat of clear arcylic.

Thus, the process uses a camera to take pictures of the natural eye and then projects the resulting pictures on a screen with color enhancement to obtain the correct shades and color for the prosthetic. The computer enhancement and printing of the natural eye color information on a material that is stable with acrylics make it possible to obtain an exact duplicate of the natural eye compared to any hand painting attempt at reproduction. Moreover, the process shortens the time involved for completion of the prosthesis.

The information obtained from the natural eye can be stored and reproduced whenever required.

DETAILED DESCRIPTION OF THE INVENTION

In actual practice, essentially all of the steps required for fitting a prosthetic eye for a patient can be accomplished during two appointments rather than a minimum of three appointments as previously required.

According to the invention, the patient is present for an impression and evaluation during the first appointment. This part of the office visit involves obtaining an impression of the missing eye socket, evaluation of the soft tissue, and placing a wax try in for proper aperture and centering.

According to the invention, a high resolution camera (e.g. Minolta RD 175) is used to take a picture of the natural eye and this information is fed into a computer (e.g. Sony High Resolution computer) so as to create a permanent file of color and appearance of the natural eye. Multiple shots of the iris, sclera, etc. of the patient's natural eye are taken with a digital camera and the pictures are projected on a screen with computer enhancement to verify shades and color with patient present. This is accomplished during the first appointment along with the impression and evaluation of the missing eye socket. At this point, the patient can be discharged.

Following the patient's first appointment, the scleral base is made and then the computer enhanced picture of the natural eye is printed on an acrylic compatible material. This is then placed in the scleral base and a finishing coat of clear acrylic is placed over the top and then highly contoured and polished to form the finished prosthetic. The prosthetic eye thus produced is of superior quality and exceptional appearance.

The finished prosthetic product is then delivered to the patient during a second appointment with final adjustments as needed.

DESCRIPTION OF THE DRAWINGS

For a better understanding of the objects and techniques of the invention reference should be made to the following detailed description and accompanying drawing wherein.

The FIGURE is a schematic diagram illustrating an imaging color system for producing an ocular prosthesis matching in appearance to a natural eye.

Referring now to the FIGURE, an imaging color sensor or device for measuring the color of a natural eye 10 comprises a camera 15, a light source 20 and a signal processor 25 or computer. The camera can be a still camera or a video camera providing analog or digital electrical signals to processor 25. The color signals for the natural eye viewed with the camera are transmitted to processor 25 and stored.

As illustrated, light source 20 may illuminate the natural eye whose color is to be measured. Any light source will suffice, such as, for example, a light bulb or light projector. However, the light source is not necessary.

Camera 15, in this embodiment, a Minolta RD 175, is adapted to transform received light into electrical signals providing color information taken from natural eye 10. The transformation of received light into electrical signals providing color information is known in the art.

Signal processor 25 is coupled to camera 15 and processes the electrical signals produced by the camera to obtain the color information about the natural eye embedded in the electrical signals. In this embodiment, signal processor 25 may comprise a Sony High Resolution monitor with "Adobe Photoshop" software. The invention, however, is not limited to this particular signal processor.

Signal processor 25 is electrically coupled to a video monitor or screen 30 for viewing the results provided by the signal processor.

Signal processor 25 performs the processing of the electrical signals to adjust or compensate for various effects that may degrade the precision or quality of the color measurements obtained. The reflection of light from the natural eye, which is non planar, may affect the color measurement obtained. In the present embodiment, the natural eye is not only non planar but also includes at least two measurably different or distinct colors at two respective locations on its surface. The signal processor can be adapted to process the digital image so as to differentiate between the different colors on the natural eye at the different locations.

The color information of the natural eye 10 obtained by signal processor 25 can be transmitted to printer 35 which is typically a laser printer, such as an HP Ink Jet 610 printer, and then projected onto acrylic compatible material which is then placed on the prosthesis 40 prior to the final clear layer of acrylic. The color information imprinted on prosthetic 40 corresponds to the natural eye 10.

Those skilled in the art will readily appreciate that the present invention provides a number of advantages, namely, (1) an exact reproduction of the natural eye is obtained, (2) computer enhanced three dimension ability for a more natural appearance of the prosthetic, (3) time saving to the patient by not requiring a long appointment for painting of the prosthetic, (4) time saving of the technician for construction of the prosthetic with complicated painting trying to match the natural eye, and (5) patient file maintained for reference and reproduction whenever required.

What is claimed is:

1. A process for the production of a prosthetic eye that substantially matches the appearance and color of a patient's natural eye which comprises the steps of:
    (1) obtaining an impression of a missing eye socket and evaluating soft tissue,
    (2) positioning a wax try in the eye socket for proper aperture and centering,
    (3) taking multiple pictures of iris and sclera of the patient's natural eye with a digital camera which provides digital electrical signals to a signal process,
    (4) projecting the resulting pictures obtained by the signal process on a screen with color enhancement to obtain the correct shades and color for the prosthetic,
    (5) forming a scleral base and then laser printing the color enhanced picture of the natural eye on an acrylic compatible material, and
    (6) placing the acrylic compatible material on the scleral base and applying a finishing coat of clear acrylic and then contouring and polishing to produce the finished prosthetic.

* * * * *